(12) United States Patent
Shah et al.

(10) Patent No.: US 10,342,873 B2
(45) Date of Patent: Jul. 9, 2019

(54) VALERIAN COMPOSITION AND RELATED METHODS

(71) Applicant: Physician's Seal, LLC, Boca Raton, FL (US)

(72) Inventors: Syed M. Shah, Boca Raton, FL (US); Christopher Diorio, Boca Raton, FL (US); Daniel Hassan, Boca Raton, FL (US); Fred Hassan, Boca Raton, FL (US)

(73) Assignee: Physician's Seal, LLC, Boca Raton, FL (US)

( * ) Notice: Subject to any disclaimer, the term of this patent is extended or adjusted under 35 U.S.C. 154(b) by 0 days.

(21) Appl. No.: 15/586,709

(22) Filed: May 4, 2017

(65) Prior Publication Data

US 2017/0319697 A1 Nov. 9, 2017

Related U.S. Application Data

(60) Provisional application No. 62/332,728, filed on May 6, 2016.

(51) Int. Cl.
| | | |
|---|---|---|
| *A61K 36/00* | (2006.01) | |
| *A61K 47/12* | (2006.01) | |
| *A61K 9/00* | (2006.01) | |
| *A61K 9/20* | (2006.01) | |
| *A61K 9/28* | (2006.01) | |
| *A61K 36/35* | (2006.01) | |
| *A61K 47/38* | (2006.01) | |
| *A61K 36/84* | (2006.01) | |
| *A61K 9/24* | (2006.01) | |
| *A61P 25/20* | (2006.01) | |
| *A61P 25/22* | (2006.01) | |

(52) U.S. Cl.
CPC ............ *A61K 47/12* (2013.01); *A61K 9/0053* (2013.01); *A61K 9/209* (2013.01); *A61K 9/2013* (2013.01); *A61K 9/2054* (2013.01); *A61K 9/2086* (2013.01); *A61K 9/28* (2013.01); *A61K 36/35* (2013.01); *A61K 36/84* (2013.01); *A61K 47/38* (2013.01); *A61P 25/20* (2018.01); *A61P 25/22* (2018.01)

(58) Field of Classification Search
CPC ...................................................... A61K 36/00
USPC ........................................................ 424/725
See application file for complete search history.

(56) References Cited

U.S. PATENT DOCUMENTS

| | | | |
|---|---|---|---|
| 5,552,418 A | 9/1996 | Depreux et al. | |
| 5,840,332 A | 11/1998 | Lerner et al. | |
| 5,846,939 A | 12/1998 | Miclo et al. | |
| 5,856,529 A | 1/1999 | Catt et al. | |
| 6,034,239 A | 3/2000 | Ohkawa et al. | |
| 6,383,526 B1 | 5/2002 | Andrews et al. | |
| 7,455,864 B2 | 11/2008 | Heuer et al. | |
| 7,476,405 B2 | 1/2009 | Gardiner et al. | |
| 8,512,769 B2 | 8/2013 | Feistel et al. | |
| 8,642,648 B2 | 2/2014 | Tanoue et al. | |
| 8,785,492 B2 | 7/2014 | Dressman et al. | |
| 8,809,395 B2 | 8/2014 | Mulzer et al. | |
| 8,821,926 B2 | 9/2014 | Marunaka et al. | |
| 9,060,995 B2 | 6/2015 | Dressman et al. | |
| 2002/0132006 A1* | 9/2002 | Sue ...................... | A61K 9/2886 424/482 |
| 2005/0129783 A1 | 6/2005 | McCleary et al. | |
| 2007/0196348 A1 | 8/2007 | Gardiner et al. | |
| 2008/0299199 A1 | 12/2008 | Bar-Shalom et al. | |
| 2011/0064712 A1 | 3/2011 | Amato | |
| 2013/0116215 A1 | 5/2013 | Coma et al. | |
| 2014/0271890 A1 | 9/2014 | Ahmad | |
| 2014/0314860 A1 | 10/2014 | Shah et al. | |
| 2015/0250203 A1 | 9/2015 | Edwards et al. | |
| 2016/0067186 A1 | 3/2016 | Shah et al. | |
| 2016/0279070 A1 | 9/2016 | Gorecka et al. | |

FOREIGN PATENT DOCUMENTS

| | | |
|---|---|---|
| EP | 1743633 B1 | 8/2010 |
| WO | 2014083438 A3 | 11/2014 |

OTHER PUBLICATIONS

The International Pharmacopoeia—Sixth Edition, 2016, 1 page.*
Axel Becker et al.; "The Anxiolytic Effects of a Valerian Extract Is Based on Valerenic Acid"; BMC Complementary and Alternative Medicine; vol. 14; pp. 1-5; 2014.
Birgit M. Dietz; "Valerian Extract and Valerenic Acid are Partial Agonists of the 5-HT 5a Receptor in Vitro"; Molecular Brain Research, vol. 138; pp. 191-197; 2005.
Del Valle-Mojica:"Aqueous and Ethanolic Valeriana Officinalis Extracts Change the Binding of Ligands to Glutamate Receptors"; Hindawi Publishing Corporation; Evidence-Based Complementary and Alternative Medicine; vol. 2011, Article ID 891819.
Gail D. Anderson et al.; "Pharmacokinetics of Valerenic Acid After Single and Multiple Doses of Valerian in Older Women"; Phytotherapy Research; Phytother. Res. 24: pp. 1442-1446 2010; Published online Apr. 13, 2010 in Wiley Online Library.
M. Goppel, G. Franz; "Stability Control of Valerian Ground Material and Extracts: a new HPLC-Method for the Routine Quantification of Valerenic Acids and Lignans"; Department of Pharmaceutical Biology, Institute of Pharmacy, University of Regensburg, Germany; vol. 59, pp. 446-452; 2004.

(Continued)

*Primary Examiner* — Michael V Meller
(74) *Attorney, Agent, or Firm* — Christopher M. Ramsey; GrayRobinson, P.A.

(57) ABSTRACT

A valerian composition includes a therapeutically effective pharmaceutical dosage form having a solid core including a polymer in which valerian and a valerian stability improving amount of an acidifying agent are contained. The valerian stability improving amount of acidifying agent being sufficient to impart a pH of 2 to 5 to the polymer.

7 Claims, No Drawings

Specification includes a Sequence Listing.

(56) References Cited

OTHER PUBLICATIONS

Philipp Kirchhoff et al.: "Zinc Salts Provide a Novel, Prolonged and Rapid Inhibition of Gastric Acid Secretion"; The American Journal of Gastroenterology, vol. 106, pp. 62-70; Jan. 2011.
Rein Bos, et al.; "Analytical Aspects of Phytotherapeutic Valerian Preparations"; Phytochemical Analysis, vol. 7, pp. 143-151; 1996.
Roy Upton; "Valerian Root"; American Herbal Pharmacopoeia and Therapeutic Compendium. Apr. 1999.
Rudiger Hardeland; "New Approaches in the Management of Insomnia: Weighing the Advantages of Prolonged-Release Melatonin and Synthetic Melatoninergic Agonist"; Neuropsychiatric Disease and Treatment vol. 5, pp. 341-354; 2009.
International Search Report of Jul. 26, 2017 for PCT/US2017/031046.

* cited by examiner

VALERIAN COMPOSITION AND RELATED METHODS

CROSS-REFERENCE TO RELATED APPLICATION

This claims priority from U.S. provisional Application No. 62/332,728, filed May 6, 2016, which is incorporated by reference in its entirety.

FIELD

This relates to the field of supplement compositions and, more particularly, to valerian compositions.

SEQUENCE LISTING

The application contains a Sequence Listing electronically submitted via EFS-web to the United States Patent and Trademark Office as a text file named "Sequence_Listing.txt." The electronically filed Sequence Listing serves as both the paper copy required by 37 C.F.R. § 1.821(c) and the computer readable file required by 37 C.F.R. § 1.821(c). The information contained in the Sequence Listing is incorporated by reference herein in its entirety.

BACKGROUND

Valerian (*Valerians officianalis*) is a plant that has been used as an herbal remedy for centuries. Its root extracts have been proposed for use as a sedative, anxiolytic, muscle relaxer, and an anticonvulsant. Valerian root and extracts thereof are currently available as dietary supplements.

Valerian contains a number of compounds that may be responsible for its therapeutic activity, but it is not fully understood which is the primary contributor. These compounds include: valerenic acid and derivatives thereof, including acetoxyvalerenic acid and hydroxyvalerenic acid; kessane derivatives valeranone and valerenal; valeric acid; valproic acid; and valepotriate compounds. It has been shown that valerian's effects are mediated through the brain's GABA receptors, which respond to the neurotransmitter gamma-aminobutyric acid. These are the same receptors that benzodiazepine drugs target.

Quality concerns have been reported for several commercially available valerian formulations. ConsumerLab.com tested several products for valerenic acid content and found that at the time of testing some of those products had either no detectable valerenic acid or an amount that is less than what the label specifies. This may suggest that the valerenic acid has a limited shelf life.

BRIEF SUMMARY

A valerian-containing pharmaceutical dosage form composition is described here.

A first example of the composition comprises a therapeutically effective pharmaceutical dosage form having a solid core including a polymer in which valerian and aN amount of acidifying agent are contained. The amount of acidifying agent is sufficient to impart a pH of 2 to 5 to the polymer.

A second example of the composition comprises a therapeutically effective pharmaceutical dosage form having a solid core including valerian within an acidified polymer matrix, an expedited release portion, and a sustained release portion. The expedited release portion includes a first fraction of valerian and is effective to release the first fraction of the valerian within about 2 hours from placement in a 0.1 N HCl solution. The sustained release portion includes a second fraction of valerian, the sustained release portion being effective to release the second fraction within about 10 hours from placement in a phosphate buffer with a pH of 6.8.

An example of a method of making a storage stable valerian pharmaceutical dosage form comprises forming an acidified polymer matrix by combining valerian, a hydrogel forming polymer, an amount of acidifying agent acidifying agent, and water; and making a solid pharmaceutical dosage including the acidified polymer matrix. The amount of acidifying agent makes the solid pharmaceutical dosage form storage stable by preventing degradation of the valerian when the pharmaceutical dosage form is stored at 25 degrees C. and 60% relative humidity.

An example of a method of treatment comprises administering to a patient in need thereof a therapeutically effective amount of a pharmaceutical dosage form having a solid core including a polymer in which valerian and a valerian stability improving amount of acidifying agent are contained, the valerian stability improving amount of acidifying agent being sufficient to impart a pH of 2 to 5 to the polymer.

The following additional features may be included in any of these examples of compositions and methods.

The composition may be an oral pharmaceutical dosage form so that administration may be performed orally.

The pharmaceutical dosage form may be at least one oral dosage form selected from a tablet, capsule, and a multiparticulate.

The valerian stability improving amount of acidifying agent may make the pharmaceutical dosage form storage stable by preventing degradation of the valerian when the pharmaceutical dosage form is stored at 25 degrees C. and 60% relative humidity.

The valerian stability improving amount of acidifying agent may be sufficient to impart a pH of 3 to 5 to the polymer.

The expedited release portion may include 5% to 50% of the valerian in the pharmaceutical dosage form and may be effective to release the valerian therein within about 2 hours from placement in a 0.1 N HCl solution.

The sustained release portion may include the remainder of the valerian in the pharmaceutical dosage form and may be effective to release the valerian therein within about 10 hours from placement in a phosphate buffer with a pH of 6.8.

The polymer may be a hydrogel forming polymer that swells upon absorption of water.

The therapeutically effective amount may include about 150 mg to about 250 mg of valerian.

Valerian may be 15% w/w to 45% w/w of the pharmaceutical dosage form

The acidifying agent may be 1% w/w to 20% w/w of the pharmaceutical dosage form.

The polymer may be 1% w/w to 15% w/w of the pharmaceutical dosage form.

The composition may be used to treat a target physiological condition such as pain, insomnia, anxiety, and/or a melatonin deficiency among others.

DETAILED DESCRIPTION OF EXAMPLE EMBODIMENTS

The term "valerian" as used herein includes valerian root, valerian extracts, and/or the therapeutically active compounds in valerian such as valerenic acid and/or valepotriates such as valtrate and didrovaltrate. Valerian may be in a dried root, powder, or liquid form. The liquid form contains the active components of the valerian root suspended in a solvent. Alcohols are typically used as the extraction solvent, but the liquid form may also be an oil.

In conventional aqueous or hydroalcoholic extracts or tinctures of valerian, the primary water-soluble active compound has been reported to be isovaleric acid. Ammonium isovalerate and isovaleramide are produced in ammoniated tinctures. Valepotriates and monoterpene isovalerate esters, such as bornyl and lavandulyl isovalerates, are reported to act as prodrugs for isovaleric acid, its salts, and isovaleramide.

A first example embodiment of the valerian product includes a valerian-containing pharmaceutical dosage form in which valerian is in a polymer matrix with an acidic pH. The acidic pH helps stabilize some of the bio-active compounds in valerian to enhance the storage stability of the valerian product.

The acidic pH is provided by an acidifying agent in a valerian stability improving amount. A valerian stability improving amount may be, for example, the amount of acidifying agent needed to improve the storage stability of the valerian product as measured by an objective measure of valerian storage stability.

Many conventional techniques have been reported for measuring valerian's storage stability. One such technique, reported by Goppel and Franz titled "Stability control of valerian ground material and extracts: a new HPLC-method for the routine quantification of valerenic acids and lignans" was published in *Pharmazie* Vol. 59 pages 446-452 in 2004. According to this report, valerian's storage stability can be measured by monitoring the content of valerenic acids and lignans. Hydroxyvalerenic acid, pinoresinol, and hydroxypinoresinol were identified as degradation products. The storage conditions were 25 degrees C./60% relative humidity, 30 degrees C./60% relative humidity, and 40 degrees C./75% relative humidity. Goppel and Franz measured the storage stability using a high performance liquid chromatography (HPLC) technique combined with spectrophotometry.

A significant increase in the amount of hydroxyvalerenic acid during the tests was shown to be a positive indicator for a lack of storage stability.

Other techniques for measuring the storage stability of valerian may include chromatographic chemical fingerprint methods such as gas chromatography and thin layer chromatography combined with spectrophotometry.

The pharmaceutical dosage form may be an oral dosage form such as a tablet, caplet, capsule, multiparticulate, or the like. In such cases the dosage form has a solid core containing one or more of the active ingredients, including valerian, within a polymer matrix.

The polymer matrix is formed from at least one pharmaceutically acceptable polymeric excipient. Examples of polymeric excipients include, but are not limited to: cellulosic polymers such as carboxymethylcelluloses, methylcelluloses, hydroxypropylcelluloses, and hydroxypropylmethylcelluloses; hyaluronates; alginates; polysaccharides, heteropolysaccharides, pectins; poloxamers; poloxamines; ethylene vinyl acetates; polyethylene glycols; dextrans; polyvinylpyrrolidones; chitosans; polyvinylalcohols; propylene glycols; polyvinylacetates; phosphatidylcholines, lecithins; miglyols; polylactic acid; polyhydroxybutyric acid; mixtures thereof, copolymers thereof, derivatives thereof, and the like.

In a particular example, the at least one polymeric excipient is a hydrogel-forming polymer. A hydrogel-forming polymer is a polymer capable of swelling by absorbing water. When ingested by a patient, the hydrogel-forming polymer absorbs water and swells. The active ingredient(s) in the core disperse through the formed hydrogel and gradually exit the hydrogel into the patient's gastrointestinal ("GI") tract. The hydrogel-forming polymer may act as a release-controlling polymer to provide a sustained release of active ingredient(s) into the GI tract over a desired time period.

Hydroxypropyl methylcellulose ("HPMC" or "hypromellose") is used in certain particular formulations of the dosage form because it forms a hydrogel and is available in many different versions that vary by molecular weight. Thus the properties of the dosage form can be varied by selecting different a different molecular weight version of HPMC.

The polymeric matrix may function to prevent oxidative degradation of valerian. It provides a moisture and oxygen barrier during storage, which substantially prevents moisture and oxygen from penetrating into the dosage form.

The acidic pH is imparted to the polymer matrix by blending an acidifying agent such as an acid and/or an acidic buffer with the polymeric excipient. Examples of acidifying agents include, but are not limited to, acidic molecules including organic and/or inorganic acidic molecules. Organic acidic molecules include, but are in no way limited to, low molecular weight carboxylic acids such as citric acid, succinic acid, and tartaric acid. Inorganic acidic molecules include phosphoric acid and hydrochloric acid, for example. Acidic buffers can be prepared with organic or inorganic acidic molecules. Acidic buffers such as mono sodium citrate or mono potassium phosphoric acid (monopotassium phosphate) are examples, but acidic buffers are in no way limited to these.

Although not intended to be bound by theory, it is believed that one of the valerian degradation pathways is decarboxylation of the carboxylic acids, such as valerenic acid. Using a carboxylic acid-based acidifying agent may help mitigate decarboxylation. Because decarboxylation may become favorable at elevated temperatures, it is believed that a carboxylic acid-based acidifying agent may improve the storage stability of valerian.

The amount of acidifying agent is sufficient to impart an acidic pH to the polymer matrix when it absorbs water and swells. Some suitable pH ranges for the polymer matrix include 0.1 to 7, 0.1 to 6, 0.1 to 5, 1 to 6, 1 to 5, 2 to 6, 2 to 5, 2.5 to 5.5, 2 to 4.5, 3 to 6, 3 to 5, 3 to 4.5, 3.3 to 5, or 3.4-4.5.

The pKa of valerenic acid and valproic acid is reported to be about 5. In some examples of the product, it is desirable to use sufficient acidifying agent to impart a pH of 5 or below in order to maintain valerenic acid and valproic acid their protonated forms. It is believed that imparting such a pH to the polymer matrix will help prevent oxidative degradation to these acids.

A second embodiment of the valerian product includes the valerian-containing pharmaceutical dosage form just discussed, but in which melatonin is included in the polymer matrix with valerian. In this embodiment it may be desirable to use sufficient acidifying agent to impart a pH of 4.4 or below to the polymer matrix. Examples of such pH ranges include 0.1 to 4.4, 1 to 4.4, 2 to 4.4, 3 to 4.4, 4 to 4.4, 1 to 4, 2 to 4, or 3 to 4. In this pH range the solubility of melatonin is enhanced compared to a neutral pH.

This may be useful for obtaining a sustained release of melatonin throughout the GI tract. Melatonin is much more soluble in the stomach than the intestines because the pH of the stomach is low whereas the pH of the intestines is higher. The acidified polymer matrix forms a controlled pH carrier for the melatonin within the GI tract. Melatonin remains solubilized in the matrix when it absorbs water in the GI tract and can gradually release from the matrix as the dosage form passes through the GI tract, regardless of the GI tract's local pH environment.

In this second embodiment, the dosage form provides a sustained release of valerian and melatonin. Such a product is useful as a sleep aid with dual therapeutic functionality. The valerian will act as a sedative, helping the patient relax prior to falling asleep. The melatonin will help the patient fall asleep and stay asleep through the night.

Melatonin has been reported to have a pKa of approximately 4.4 to 4.7. This gives melatonin different degrees of dissociation and different solubilities as it travels through the GI tract due to pH changes. In the gastric environment, at a pH range of approximately 1 to 3, its solubility is relatively high. In the upper GI tract environment, at a pH range of approximately 4.5 to 5.5, its solubility decreases. In the lower GI tract environment, at a pH range of approximately 5.5 to 7, its solubility decreases even further. This variability in the GI tract pH is not a major factor for conventional immediate-release melatonin dosage forms, as melatonin is readily dissolved in the low pH of the gastric environment. Unfortunately, this results in the melatonin being absorbed and eliminated too quickly to mimic the pattern of the endogenous melatonin found in healthy young subjects.

The dosage forms including melatonin are adapted to release an effective amount of valerian and melatonin within the pH range found in the intestines continuously for at least 3 and up to 10 hours. In a particular example, the dosage form is adapted to release melatonin over a period of 3-10 hours after ingestion regardless of the pH environment it passes through. This sustained release of valerian and melatonin will help the subject remain asleep through the night.

The polymeric matrix effectively insulates the melatonin and valerian from the pH environment of the GI tract. Instead of dissolving directly into the GI tract, the melatonin and valerian dissolve within the polymeric matrix, forming a concentration gradient across the matrix. Melatonin and valerian will then be released into the GI tract from the periphery of the matrix in this manner.

A third embodiment of the valerian-containing product includes valerian and melatonin together in the polymer matrix with an acidic pH, but the dosage form also includes at least one analgesic ingredient. This embodiment provides three therapeutic benefits because the analgesic ingredient will further provide pain relief.

Examples of analgesic ingredients include, but are not limited to salicin, acetylsalicylic acid, sodium salicylate, acetaminophen, ibuprofen, diclofenac, ketoprofen, bromelain, and naproxen.

In a particular example of the dosage form, the analgesic ingredient is a salicin source, such as willow bark (*Salix* spp.) or willow bark extract. Salicin is pain relieving anti-inflammatory compound similar in structure to acetylsalicylic, which is the active ingredient in Aspirin. Willow bark may also contain other flavonoids that are analgesic ingredients. Willow bark has been used to treat headaches, muscle pain, and arthritis among many other conditions.

The salicin source may contain willow bark from one or more willow species. There are various types of willow bark that contain salicin, including bark from the white willow (*Salix alba*), black willow (*Salix nigra*), crack willow (*Salix fragilis*), purple willow (*Salix purpurea*), and weeping willow (*Salix babylonica*). The amount of salicin in the willow bark varies amongst species and age of the tree. If white willow bark is the salicin source, it may be desirable to choose a white willow bark extract containing at least 75%, 85%, or 95% salicin.

The dosage form may include at least one sedative ingredient in combination with valerian. Such sedative ingredients may include a skeletal muscle relaxer, and/or a GABA modulator. Examples of sedative ingredients include, but are not limited to, L-theanine, lemon balm, skullcap, and a decapeptide having the amino acid sequence Tyr-Leu-Gly-Tyr-Leu-Glu-Gln-Leu-Leu-Arg (SEQ ID NO: 1 YLGYLEQLLR), which is marketed as LACTIUM® (Ingredia Societe AnonymeFrance) and described in U.S. Pat. No. 5,846,939.

If the dosage form includes L-theanine, 25-250 mg, 50-200 mg, or about 100 mg may be used.

If the dosage form includes skullcap, 25-250 mg, 50-200 mg, or about 100 mg may be used.

If the dosage form includes lemon balm, 25-250 mg, 50-200 mg, or about 100 mg may be used.

If the dosage form includes the decapeptide, 25-250 mg, 50-200 mg, or about 100 mg may be used.

In the products discussed above the dosage form includes a sustained release portion, which is the polymer matrix containing the active ingredient(s). The sustained release portion is effective to release the active ingredient(s) therefrom into the patient's lower GI tract over about 3 hours to about 10 hours after oral ingestion by the patient. In certain cases, the dosage form will release substantially all of the active ingredient(s) therefrom within 10 hours after oral ingestion or within about 8 hours after oral ingestion.

The dosage form may also include an expedited release portion. The expedited release portion is effective to release about 50% of the active ingredient(s) into the lower GI tract within about 2 hours after oral ingestion or about 1 hour after oral ingestion.

The expedited release portion of the dosage form can be formulated many different ways. A few examples are described below, but these examples are not an exhaustive list of the many possibilities.

In the first, second, and third embodiments discussed above, the polymer matrix may function as both the expedited release portion and sustained release portion. This is because when the dosage form reaches the patient's stomach, it will begin releasing some of the active ingredients from the polymer matrix almost immediately as the polymer matrix absorbs water in the stomach. As the polymer matrix swells, a pH gradient forms within the matrix and the release rate of the active ingredient(s) slows.

Another example of a dosage form with an expedited release portion and sustained release portion is a bi-layer tablet having one layer forming the sustained release portion and another layer forming the expedited release portion.

Another example of a dosage form with an expedited release portion and sustained release portion is a capsule containing the sustained release portion and expedited release portion. In such an example, the expedited release portion may include particulates effective to release the active ingredients therein over a desired expedited time period and the sustained release portion may be another set of particulates effective to release the active ingredients therein for a sustained time period.

Another example of a dosage form with an expedited release portion and sustained release portion is a tablet or capsule in which the polymer matrix forms a solid core and the expedited release portion is in a coating over the core.

The relative dosage percentage of the expedited and sustained release portions can vary. In some examples, the expedited release portion contains 5% to 50% or up to 65% of a particular active ingredient in the dosage form. In other examples, the sustained release portion contains up to 90% of a particular active ingredient in the dosage form. In another example, the expedited release portion contains approximately 50% of the active ingredient(s). The active ingredients from the expedited release portion are released approximately in the first two hours after ingestion. The active ingredients in the sustained release portion include the remainder of the active ingredient(s), which are released approximately over the next 5-8 hours or within about 10 hours after ingestion.

The release profile may be measured by simulating the GI tract environment by placing the dosage form in a 0.1 N HCl (hydrochloric acid) solution for two hours, then placing it in a phosphate buffer solution of pH=6.8 for 12 hours.

The release rate of the active ingredient(s) from the dosage form can be controlled in several ways. The concentration of the active ingredient(s) may be adjusted. The pH of polymer matrix may be adjusted. One or more release rate controlling coatings may be included. The thickness of such a coating may be adjusted. The size and shape of the dosage form may also be adjusted to provide the preferred release rate.

An effective amount is an amount that is sufficient to provide a therapeutic benefit affecting a disease or condition in the body.

A therapeutically effective amount of valerian, melatonin, and/or analgesic ingredient may be 1-1,000 mg/day, including 1-25 mg/day, 25-50 mg/day, 50-75 mg/day, 75-100 mg/day, 100-150 mg/day, 150-200 mg/day, 200-250 mg/day, 250-300 mg/day, 300-350 mg/day, 350-400 mg/day, 400-450 mg/day, 450-500 mg/day, 500-550 mg/day, 550-600 mg/day, 600-650 mg/day, 650-700 mg/day, 700-750 mg/day, 750-800 mg/day, 800-850 mg/day, 850-900 mg/day, 900-950 mg/day, 950-1,000 mg/day. Higher doses (1,000-3,000 mg/day) might also be effective. The weight in mg is often calibrated to the body weight of the patient in kg, thus these example doses may also be written in terms of mg/kg of body weight per day.

In practice, the therapeutically effective amount may vary depending on numerous factors associated with the patient, including age, weight, height, severity of the condition, administration technique, and other factors. The therapeutically effective amount administered to a patient may be determined by medical personnel taking into account the relevant circumstances.

The therapeutically effective amount may be determined or predicted from empirical evidence. Specific dosages may vary according to numerous factors and may be initially determined on the basis of experimentation.

The product may be administered as a single dose or as part of a dosage regimen. For a dosage regimen, the therapeutically effective amount is adjustable dose to dose to provide a desired therapeutic response.

Multiple doses may be administered at a predetermined time interval and subsequent doses may be proportionally reduced or increased, depending on the situation.

Table 1 is a list of a few of the possible therapeutically effective amounts of active ingredients in several examples of the valerian-containing product, Examples A-H. Here, the mass is reported by weight of a unitary dosage form. This list is not meant to be exhaustive.

TABLE 1

Amounts of active ingredient(s) in examples of the valerian-containing product.

| Active | Mass (milligrams) | | | | | | | |
|---|---|---|---|---|---|---|---|---|
| | A | B | C | D | E | F | G | H |
| Valerian source | 100-400 | 150-300 | 100-400 | 150-300 | 100-400 | 150-300 | 150-250 | 190-210 |
| Melatonin | 0 | 0 | 1-10 | 3-6 | 1-10 | 3-7 | 4-6 | 4-6 |
| analgesic | 0 | 0 | 0 | 0 | 150-550 | 200-300 | 240-270 | 250-275 |

As mentioned above, the dosage form will typically be an oral dosage form such as a tablet, caplet, capsule, multiparticulate, or the like. One or more pharmaceutically acceptable excipients aside from those described already may be used to obtain the desired dosage form and give it the desired properties.

Examples of excipients include, but are not limited to, carriers, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

Tablets and caplets may be prepared using conventional tableting techniques such as dry blending or wet granulation. The dry blend or granulation may be compressed into a final tablet form.

Capsules may be prepared using different techniques. For example, dried granules produced by wet granulating the ingredients may be loaded into a capsule, such as a gelatin capsule.

A spray granulation process may be used to prepare the dosage form as well. The spray granulation process produces granular cores containing the active ingredient(s), the polymer matrix, and the acidifying agent. The granular cores may be combined into a final dosage form such as by compressing them into a tablet or loading them into a capsule, for example.

Alternatively, the capsules or sachets may be loaded with individual spheroidal multiparticulates having a diameter of from about 0.5 mm to about 4 mm or from about 0.5 mm to about 3 mm that are prepared by forming a wet mass of the ingredients, extruding the wet mass, cutting the extruded wet mass into pieces, and spheronizing the pieces. The individual particulates may include any of the coatings discussed here.

The expedited and sustained release portions may be formulated separately then combined into the final dosage form. For example, the sustained release portion can be formed from a plurality of individual granular particulates that contain the acidified polymeric matrix and active ingredients. Likewise the expedited release portion can be formed from a plurality of individual granular particulates that contain its active ingredients. If valerian and/or melatonin is(are) included in the expedited release portion, the expedited release portion may also include an acidified polymeric matrix.

When preparing the dosage form, it may be desirable to include a solubilizing agent to help solubilize the valerian and/or melatonin, if melatonin is included. Solubilizing agents include, but are not limited to, polyethylene glycol (PEG) based surfactants. The molecular weight of PEG can be chosen to provide the desired properties of the composition. A solubilizing agent may not be needed in every embodiment of the dosage form.

Conventional processing aids may be used to prepare dosage form. Examples of processing aids include, but are not limited to, magnesium stearate, stearic acid, talc, and sodium lauryl sulfate.

The dosage form may include a pharmaceutically acceptable filler. Examples of fillers include, but are not limited to, silicates, calcium carbonate, glycine, dextrin, sucrose, sorbitol, dicalcium phosphate, calcium sulfate, lactose, kaolin, mannitol, sodium chloride, talc, dry starches and powdered sugar.

The dosage form may include a pharmaceutically acceptable binder. Examples of binders include, but are not limited to, cellulosic, and povidone binders such as microcrystalline cellulose, hydroxypropyl methylcellulose, and crospovidone.

The dosage form may be coated to aid in swallowing, to mask the taste of the ingredients, improve appearance, to protect the dosage form from moisture, and/or to have an enteric coating. The coating may be applied using conventional coating techniques, such as, for example, spray coating, bed coating, or the like.

The dosage form may be coated with an enteric coating to substantially prevent the active ingredients from releasing into the stomach. Examples of enteric coating materials include shellac, cellulose acetate phthalate, polyvinyl acetate phthalate, ethyl cellulose/sodium alginate, hypromellose acetate succinate, or a methacrylic acid-based polymer or co-polymer such as methacrylic acid-ethyl acrylate copolymer.

The dosage form may be coated with a seal coating. Examples of seal coating materials include, but are not limited to, hydroxypropyl cellulose, hypromellose, and polyvinyl alcohol. A particular example of the seal coating is OPADRY Clear, which contains, HPMC and polyethylene glycol.

Valerian has been reported to have both a foul smell and taste. If desired, the dosage form may include a taste and/or smell-masking coating.

Valerian also contains volatile components, which may evaporate and leave the dosage form during storage. An evaporation-preventative coating may be applied over the core to minimize evaporation of these components. An example of such an evaporation-preventative coating is a gelatin coating. In some cases, acid bone gelatin may be a desirable source of gelatin.

Examples of dispersing agents include, but are not limited to, copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of N-vinyl purine or pyrimidine derivatives and N-vinylpyrrolidone.

Several particular examples of the valerian product will now be described. The scope of possible embodiments, however, is not limited to these examples. These examples are presented as percent by weight (% w/w) of the specified ingredient relative to the dosage form. If a coating is placed over the dosage form, the % w/w is the pre-coating % w/w. Any combination of the ingredients in the % w/w listed below may be employed.

Valerian may be 10%-50% w/w, 15%-45% w/w, 15%-40% w/w, 15%-35% w/w, 15%-25% w/w, 18%-24% w/w, or 20%-22% w/w.

The polymer excipient may be 0.5%-20% w/w, 1%-20% w/w, 1%-15% w/w, 1%-7% w/w, 1%-5% w/w, 2%-6% w/w, or 2%-4% w/w.

The acidifying agent may be 0.5%-20% w/w, 1%-20% w/w, 1%-15% w/w, 5%-15% w/w, 2%-10% w/w, 7%-15% w/w, 6%-10% w/w, or 7%-9% w/w.

The binder may be 0.5%-20% w/w, 2%-15% w/w, 9%-33% w/w, 10%-20% w/w, 12%-20% w/w, 12%-18% w/w, or 15%-17% w/w.

Melatonin may be 0.1%-5% w/w; 0.1%-2% w/w, 0.1% to 1% w/w, or 0.2%-0.7% w/w.

The analgesic ingredient may be 15%-60% w/w, 15%-50% w/w, 20%-60% w/w, 20%-55% w/w, 25%-35% w/w, or 26%-30% w/w.

A first example of the valerian product includes: about 15% to about 45% w/w of valerian; about 1% to about 15% w/w of acidifying agent; about 1% to about 15% w/w of hydrogel-forming polymer; and about 10% to about 20% binder.

A second example of the valerian product contains melatonin and includes: about 15% to about 45% w/w of valerian; about 0.1% to about 2% w/w melatonin; about 1% to about 15% w/w of acidifying agent; about 1% to about 15% w/w of hydrogel-forming polymer; and about 10% to about 20% binder.

A third example of the valerian product contains melatonin and a salicin source and includes: about 15% to about 45% w/w of valerian; about 0.1% to about 2% w/w melatonin; about 20% w/w to about 55% w/w salicin source; about 1% to about 15% w/w of acidifying agent; about 1% to about 15% w/w of hydrogel-forming polymer; and about 10% to about 20% binder.

In a fourth example, the valerian product includes a pharmaceutical dosage form that has a solid core including valerian dispersed within a first acidified polymeric matrix having a pH of about 1 to about 5 or about 1 to about 4.4. An expedited release portion of the dosage form includes 5% to 50% of the valerian in the dosage form. The expedited release portion is effective to release substantially all of the valerian therein within about 2 hours from placement in a 0.1 N HCl solution. A sustained release portion of the dosage form includes the remainder of the of valerian in the pharmaceutical dosage form, the sustained release portion being effective to release substantially all of the GABA receptor agonist ingredient therein within about 10 hours from placement in a phosphate buffer with a pH of 6.8.

In a fifth example, the valerian product includes a pharmaceutical dosage form that has a solid core including a combination of valerian and melatonin dispersed within a first acidified polymeric matrix having pH of about 1 to about 5 or about 1 to about 4.4. An expedited release portion of the dosage form includes 5% to 50% of the valerian and the melatonin in the dosage form. The expedited release portion is effective to release substantially all of the valerian and melatonin therein within about 2 hours from placement in a 0.1 N HCl solution. A sustained release portion of the dosage form includes the remainder of the valerian and melatonin in the dosage form. The sustained release portion is effective to release substantially all of the valerian and melatonin therein within about 10 hours from placement in a phosphate buffer with a pH of 6.8.

The following features may be included in the fifth example or any other of the examples.

The sustained release portion may include a plurality of individual granules that have the remainder of the valerian in the pharmaceutical dosage form therein.

The composition may further include an analgesic ingredient in the expedited release portion.

The pharmaceutical dosage form may be at least one of a compressed tablet, capsule, and multiparticulate-containing oral dosage form.

In the expedited release portion, the 5% to 50% of the GABA receptor agonist ingredient in the pharmaceutical dosage form may be located within a second acidified polymeric matrix having a pH of about 1 to about 5 or about 1 to about 4.4.

In a sixth example, the valerian product includes a pharmaceutical dosage form having a solid core that includes an analgesic ingredient and valerian. The valerian is dispersed within a first acidified polymeric matrix having a pH of about 1 to about 5 or about 1 to about 4.4. An expedited release portion of the dosage form includes 5% to 50% of the analgesic ingredient and valerian in the dosage form. The expedited release portion is effective to release substantially all of the analgesic ingredient and valerian therein within about 2 hours from placement in a 0.1 N HCl solution. A sustained release portion of the dosage form includes the remainder of the analgesic ingredient and valerian in the dosage form. The sustained release portion is effective to release substantially all of the analgesic ingredient and valerian therein within about 10 hours from placement in a phosphate buffer with a pH of 6.8.

The following features may be included in the sixth example or any other example.

The sustained release portion may include a plurality of individual granules that have the remainder of the valerian in the pharmaceutical dosage form therein.

The composition may further include melatonin in the acidified polymeric matrix.

The analgesic ingredient may include a salicin source. The salicin source may be a white willow bark extract that is at least about 75% salicin.

The pharmaceutical dosage form may be at least one of a compressed tablet, capsule, and multiparticulate-containing oral dosage form.

In the expedited release portion, the 5% to 50% of the analgesic ingredient in the dosage form may be located within a second acidified polymeric matrix having a pH of about 1 to about 5 or about 1 to about 4.4.

In a seventh example, the valerian product includes a pharmaceutical dosage form having a solid core that includes an analgesic ingredient, valerian, and melatonin. The valerian and melatonin are dispersed within a first acidified polymeric matrix having a pH of about 1 to about 5 or about 1 to about 4.4. An expedited release portion of the dosage form includes 5% to 50% of the analgesic ingredient, melatonin, and valerian in the dosage form. The expedited release portion is effective to release substantially all of the analgesic ingredient, melatonin, and valerian therein within about 2 hours from placement in a 0.1 N HCl solution. A sustained release portion of the dosage form includes the remainder of the analgesic ingredient, melatonin, and valerian in the dosage form. The sustained release portion is effective to release substantially all of the analgesic ingredient, melatonin, and valerian therein within about 10 hours from placement in a phosphate buffer with a pH of 6.8.

The following features may be included in the seventh example or any other example.

The analgesic ingredient may be a salicin source such as a white willow bark extract that is at least about 75% salicin.

The pharmaceutical dosage form may be at least one of a compressed tablet, capsule, and multiparticulate-containing oral dosage form.

In the expedited release portion, the 5% to 50% of the valerian and melatonin in the dosage form is located within a second acidified polymeric matrix having a pH of about 1 to about 5 or about 1 to about 4.4.

The sustained release portion may include a plurality of individual granules that have the remainder of the valerian and melatonin in the pharmaceutical dosage form therein.

Any of the example compositions may be employed in a method of treating a patient in need thereof by administering an effective amount of the composition to the patient.

The valerian product in any of the forms described above may be used to treat one or more conditions such as pain, insomnia, anxiety, melatonin deficiency, a sleep disorder, and/or a circadian rhythm disorder.

A patient in need of treatment may be treated by administering at least one of the valerian products described above to the patient. The product may be administered orally. The patient may be a human or animal patient.

The product that contains valerian in combination with melatonin and a salicin source is particularly useful for treating multiple symptoms. For example, a person experiencing pain may have trouble sleeping. The combination product may reduce the pain and help the person fall asleep.

EXAMPLES

This section describes a few specific examples of the composition. These examples are presented by way of example only and are not intended to limit the scope of the possible embodiments.

Example 1

In this example, the valerian product is prepared as a two-part dosage form. The dosage form includes an expedited release portion and a sustained release portion. The contents of the valerian product are summarized in Table 2. SR indicates that the ingredient is part of the sustained release portion. ER indicates that the ingredient is part of the expedited release portion.

TABLE 2

Contents of dosage form

| Portion | Ingredient | Mass (mg) | % w/w of portion | % w/w of dosage form |
|---|---|---|---|---|
| SR intragranular | Valerian root extract | 200 | 39.1 | 21 |
| SR intragranular | melatonin | 5 | 0.1 | 5 |
| SR intragranular | Hypromellose (PHARMACOAT® 615) | 28 | 5.5 | 3 |
| SR intragranular | Citric acid | 75 | 14.7 | 8 |

TABLE 2-continued

Contents of dosage form

| Portion | Ingredient | Mass (mg) | % w/w of portion | % w/w of dosage form |
|---|---|---|---|---|
| SR extragranular | MCC | 150 | 29.4 | 16 |
| SR extragranular | Hypromellose (METHOCEL ® K4M) | 50 | 9.8 | 5.4 |
| SR extragranular | Silicon dioxide | 2.5 | 0.49 | 0.27 |
| | | 510.5 | | |
| ER extragranular | WWB extract | 263 | 62.5 | 28 |
| ER extragranular | Silicified MCC | 150 | 35.7 | 16 |
| ER extragranular | Mg stearate | 7.5 | 1.8 | 0.8 |
| | | 420.5 | | |
| TOTAL WEIGHT | | 931 | | |

The sustained release portion is prepared via a spray granulation process, such as top spray or tangential spray fluidized bed granulation process. In this process, granules containing the valerian root extract, melatonin, and PHARMACOAT® 615 hypromellose are prepared. The pH of the granules is between 3.3-5. The microcrystalline cellulose (MCC), METHOCEL® K4M hypromellose and silicon dioxide are external to the granules.

In the sustained release portion, intragranular hypromellose provides the polymer matrix and also functions as a moisture and oxygen barrier to prevent oxidative degradation of the melatonin and valerian root extract.

The expedited release portion is designed to release about 10% to about 25% of the valerian root extract and melatonin within about one after oral ingestion and the remaining melatonin and valerian over the following 5 to 7 hours after oral ingestion.

The expedited release portion is prepared by combining the 98% salicin white willow bark extract, silicified MCC and magnesium stearate. The expedited release portion is designed to release substantially all of the white willow bark extract without about 30 minutes to 1 hour after oral ingestion.

The expedited release and sustained release portions are compressed together into a bi-layer tablet or compressed individually to form two smaller tablets. The tablets are finish coated with hypromellose or polyvinylpyrrolidone for further stability protection and to help with swallowing.

Example 2

The product in this example is similar to that of Example 1, except that the expedited release portion includes granules including the valerian root extract, PHARMACOAT® 615 hypromellose, and citric acid. The contents of this valerian product are summarized in Table 3.

TABLE 3

Contents of dosage form

| Portion | Ingredient | Mass (mg) | % w/w of portion | % w/w of dosage form |
|---|---|---|---|---|
| SR intragranular | Valerian root extract | 100 | 25.9 | 10 |
| SR intragranular | melatonin | 5 | 0.1 | 0.5 |
| SR intragranular | Hypromellose (PHARMACOAT® 615) | 14 | 36 | 1.4 |
| SR intragranular | Citric acid | 65 | 16.8 | 6.6 |
| SR extragranular | MCC | 150 | 29.4 | 16 |
| SR extragranular | Hypromellose (METHOCEL® K4M) | 50 | 9.8 | 5.4 |
| SR extragranular | Silicon dioxide | 2.5 | 0.49 | 0.27 |
| | | 386.5 | | |
| ER intragranular | Valerian root extract | 100 | 17 | 10 |
| ER intragranular | Hypromellose (PHARMACOAT® 615) | 14 | 23 | 1.4 |
| ER intragranular | Citric acid | 65 | 11 | 6.6 |
| ER extragranular | WWB extract | 263 | 62.5 | 28 |
| ER extragranular | Silicified MCC | 150 | 35.7 | 16 |
| ER extragranular | Mg stearate | 7.5 | 1.8 | 0.8 |
| | | 599.5 | | |
| TOTAL WEIGHT | | 986 | | |

Compared to the product in Example 1, this valerian product shifts half of the valerian dose to the expedited release portion.

The expedited release portion is designed to release substantially all of the white willow bark extract and valerian root extract in it within about 30 minutes to 1 hour after oral ingestion.

Example 3

The product in this example is a particular example of a bi-layer tablet dosage form, including a sustained release layer and an expedited release layer. The contents of the valerian product are summarized in Table 4.

TABLE 4

Contents of dosage form

| | | Ingredient | Mass (mg) | % w/w of Dosage form | Range (mg) |
|---|---|---|---|---|---|
| Layer one Sustained Release | intra-granular | melatonin | 5 | 0.51 | 1-10 |
| | | hypromellose (PHARMACOAT® 615) | 14 | 1.4 | 7-20 |
| | | citric acid | 65 | 6.6 | 15-85 |
| | extra-granular | microcrystalline cellulose | 150 | 15 | 100-300 |

TABLE 4-continued

Contents of dosage form

|  |  | Ingredient | Mass (mg) | % w/w of Dosage form | Range (mg) |
|---|---|---|---|---|---|
|  |  | Hypromellose (METHOCEL ® K4M) | 50 | 5.1 | 25-75 |
|  |  | silicon dioxide | 2.5 | .25 | 1-5 |
|  |  |  | 286.5 | 29 |  |
| Layer two Expedited Release | intra-granular | Valerian root extract | 200 | 20 | 100-200 |
|  |  | hypromellose (PHARMACOAT ® 615) | 14 | 1.4 | 7-20 |
|  |  | citric acid | 65 | 6.6 | 15-85 |
|  | extra-granular | Salicin white willow bark extract (98%) | 263 | 27 | 200-516 |
|  |  | silicified microcrystalline cellulose | 150 | 15 | 100-300 |
|  |  | magnesium stearate | 7.5 | 0.76 | 1-15 |
|  |  |  | 699.5 | 71 |  |
|  |  | Total tablet weight | 986 |  |  |

The right-most column in Table 4 provides some examples of possible ranges for each of the ingredients in Table 4.

Example 4

The product in this example is a valerian-containing tablet with a gelatin subcoat over the core and a finish coat over the subcoat. The valerian and citric acid are within the granules in the tablet. The contents of the valerian product are summarized in Table 5.

TABLE 5

Contents of dosage form

| Portion | Ingredient | mg | % w/w of dosage form | range (mg) |
|---|---|---|---|---|
| Intragranular | Valerian root extract | 400 | 43.3 | 100-500 |
|  | Silicified microcrystalline cellulose | 200 | 21.7 | 100-300 |
|  | citric acid | 65 | 7 | 15-85 |
|  | hypromellose | 50 | 5.4 | 10-100 |
| Extragranular | hypromellose | 50 | 5.4 | 10-100 |
|  | silicified microcrystalline cellulose | 150 | 16.6 | 100-300 |
|  | magnesium stearate | 7.5 | 0.8 | 1-15 |
| Subcoat | gelatin | 30% wt. gain |  | 10-40% wt. gain |
| Finish coat | polyvinyl alcohol or hypromellose color finish coat | 4% wt. gain |  | 1-6% wt. gain |
|  | Total tablet core weight | 922.5 |  |  |

The right-most column in Table 5 provides some examples of possible ranges for each of the ingredients in Table 5.

Example 5

The product in this example is a valerian-containing bi-layer tablet with a gelatin subcoat over the core and a finish coat over the subcoat. The valerian and citric acid are within the granules in the tablet. The valerian and the citric acid are also in both the expedited release layer and the sustained release layer. The contents of the valerian product are summarized in Table 6.

TABLE 6

Contents of dosage form

|  |  | Ingredient | mg | Range (mg) |
|---|---|---|---|---|
| Layer one Sustained Release | Intragranular | valerian root extract | 200 | 100-300 |
|  |  | hypromellose (PHARMACOAT ® 615) | 14 | 7-20 |
|  |  | citric acid | 65 | 15-85 |
|  | Extragranular | microcrystalline cellulose | 150 | 100-300 |
|  |  | Hypromellose (METHOCEL ® K4M) | 75 | 25-150 |
|  |  | silicon dioxide | 2.5 | 1-5 |
|  |  |  | 506.5 |  |
| Layer two Expedited Release | Intragranular | Valerian root extract | 200 | 100-300 |
|  |  | hypromellose (PHARMACOAT ® 615) | 14 | 7-20 |
|  |  | citric acid | 65 | 15-85 |
|  | Extragranular | silicified microcrystalline cellulose | 150 | 100-300 |
|  |  | magnesium stearate | 7.5 | 1-15 |
| Subcoat |  | gelatin | 30% wt. gain | 10-5-% wt. gain |
| Finish Coat |  | poly vinyl alcohol or hypromellose color coat | 4% wt. gain | 1-5% wt. gain |
|  |  |  | 436.5 |  |
|  |  | Total tablet weight | 943 |  |

The right-most column in Table 6 provides some examples of possible ranges for each of the ingredients in Table 6.

This disclosure has described example embodiments, but not all possible embodiments of the valerian product or associated methods. Where a particular feature is disclosed in the context of a particular embodiment, that feature can also be used, to the extent possible, in combination with and/or in the context of other embodiments. The valerian product and related methods may be embodied in many different forms and should not be construed as limited to only the embodiments described here.

That which is claimed is:

1. A tablet or capsule consisting essentially of valerian within an acidified polymer matrix, wherein the acidified polymer matrix is an acidifying agent and a polymer wherein:
   the acidifying agent is selected from the group consisting of citric acid, succinic acid, tartaric acid, phosphoric acid, and hydrochloric acid;
   the polymer is at least one hydrogel-forming polymer selected from the group consisting of a carboxymethylcellulose, a methylcellulose, a hydroxypropylcellulose, a hydroxypropylmethylcellulose, a hyaluronate, an alginate, a pectin, a poloxamer, a poloxamine, an ethylene vinyl acetate, a polyethylene glycol, a dextran, a polyvinylpyrrolidone, a chitosan, a polyvinylalcohol, a propylene glycol, a polyvinylacetate, a polylactic acid, and a polyhydroxybutyric acid; and
   the amount of acidifying agent is sufficient to impart a pH of 2 to 5 to the acidified polymer matrix.

2. The tablet or capsule of claim 1, wherein the amount of acidifying agent makes the tablet or capsule storage stable by preventing degradation of the valerian when the tablet or capsule is stored at 25° C. and 60% relative humidity.

3. The tablet or capsule of claim 1, wherein the amount of acidifying agent is sufficient to impart a pH of 3 to 5 to the polymer matrix.

4. The tablet or capsule of claim 1, wherein:
   5% to 50% w/w of the valerian is in an expedited release portion of the tablet or capsule; and
   the remaining amount of the valerian in a sustained release portion of the tablet or capsule.

5. The tablet or capsule of claim 1, which is about 150 mg to about 250 mg of valerian.

6. The tablet or capsule of claim 1, wherein:
   valerian is 15% w/w to 45% w/w of the tablet or capsule;
   the acidifying agent is 1% w/w to 20% w/w of the tablet or capsule; and
   the polymer is 1% w/w to 15% w/w of the tablet or capsule.

7. The tablet or capsule of claim 1, wherein the polymer, the valerian, and the acidifying agent are in contact with each other in the acidified polymer matrix.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 1

```
Tyr Leu Gly Tyr Leu Glu Gln Leu Leu Arg
1               5                   10
```